United States Patent [19]

Kubota et al.

[11] Patent Number: 5,148,457
[45] Date of Patent: Sep. 15, 1992

[54] SYSTEM FOR ANALYZING METAL IMPURITY ON THE SURFACE OF A SINGLE CRYSTAL SEMICONDUCTOR BY USING TOTAL REFLECTION OF X-RAYS FLUORESCENCE

[75] Inventors: Atsuko Kubota, Yokohama; Norihiko Tsuchiya, Tokyo; Shuichi Samata, Yokohama; Yoshiaki Matsushita, Yokohama; Mokuji Kageyama, Yokohama, all of Japan

[73] Assignee: Kabushiki Kaisha Toshiba, Kawasaki, Japan

[21] Appl. No.: 719,706

[22] Filed: Jun. 27, 1991

[30] Foreign Application Priority Data

Jun. 28, 1990 [JP] Japan ................ 2-170687
Apr. 17, 1991 [JP] Japan ................ 3-85469

[51] Int. Cl.⁵ ......................... G01N 23/223
[52] U.S. Cl. ......................... 378/70; 378/45; 378/79
[58] Field of Search ............ 378/44, 45, 46, 49, 378/70, 71, 73, 79, 81, 84

[56] References Cited

U.S. PATENT DOCUMENTS

| | | | |
|---|---|---|---|
| 4,169,228 | 9/1979 | Briska et al. | 378/45 |
| 4,358,854 | 11/1982 | Marten et al. | 378/45 |
| 4,847,882 | 7/1989 | Kroth et al. | 378/45 |
| 5,077,766 | 12/1991 | Schwenke et al. | 378/45 |

FOREIGN PATENT DOCUMENTS 0093355  4/1990  Japan .................. 378/45

Primary Examiner—David P. Porta
Attorney, Agent, or Firm—Foley & Lardner

[57] ABSTRACT

A system for analyzing a metal impurity at the surface of a single crystal semiconductor comprising: an incident device for allowing X-ray to be incident, at an incident angle less than a total reflection angle, onto the surface of a wafer in the form of a thin plate comprised of a single crystal semiconductor (e.g., silicon); a wafer fixing/positioning stage wherein when it is assumed that the wafer surface is partitioned by a lattice having an interval d, and that the wavelength of the X-ray from the incident device is $\lambda$, an angle that the X-ray and the wafer surface form is $\theta$, and an arbitrary integer is n, the stage is adapted to fix the crystal orientation of the wafer so as to satisfy the condition of "$2d \sin \theta \neq n\lambda$", and to allow sample points to which X-ray is incident to be subjected to positioning by a horizontal movement; and analyzing device for measuring a light quantity of a fluorescent X-ray generated as the result of the fact that the incident X-ray excites atoms at the wafer surface to analyze a quantity of the metal impurity attached on the wafer surface under the condition that the Bragg reflection causing measurement noises does not take place.

6 Claims, 7 Drawing Sheets

SYSTEM FOR ANALYZING METAL IMPURITY ON THE SURFACE OF A SINGLE CRYSTAL SEMICONDUCTOR BY USING TOTAL REFLECTION OF X-RAYS FLUORESCENCE

BACKGROUND OF THE INVENTION

This invention relates to a total reflection of X-ray fluorescence analyzing system, and more particularly to a system for allowing an X-ray to be incident below an angle of total reflection onto, e.g., a silicon (Si) wafer surface to measure a quantity of an excited fluorescent X-rays generated from metal impurity such as chrominum (Cr), iron (Fe), nickel (Ni), copper (Cu), aluminum (Al), or zinc (Zn), etc. on the surface of the wafer to analyze, on the basis of the measured result, the presence and absence of the surface metal impurity, a quantity of the attached surface metal impurity, the kind thereof, or the state of the distribution thereof, etc.

Since there are instances where metal impurities as stated above may be attached on the Si wafer in the manufacturing process, an approach is generally employed to analyze the metal impurity on the surface of the manufactured Si wafer to thereby carry out the quality control to seek for the cause of attachment thereof thus to take a measure to prevent the metal impurity from being attached.

At the beginning time when such a metal impurity analysis was conducted, an approach was employed to form a thermal oxide film of about 1000 angstroms on the Si wafer surface to take the metal impurity into the thermal oxide film to dissolve out, by acid, the thermal oxide film including the metal impurity from the Si wafer to analyze the impurity thus dissolved out by the atomic absorption method.

Thereafter, since by the development of the analyzing method, it was become unnecessary to form a thermal oxide film so that the thickness thereof is kept at about the above-mentioned value, an approach was employed to dissolve out an oxide film including metal impurity of about 30 angstroms naturally grown on the wafer surface to analyze the dissolved oxide film including metal impurity.

However, in the case of the above-mentioned analyzing method, since hydrofluoric acid (HF) vapor or nitric acid (HNO$_3$) is used as an acid for dissolving the oxide film, there exists the problem that there is the extremely high possibility that an operator may be harmed by vapor.

In view of this, an analyzing method was conventionally developed to allow X-ray to be incident onto the surface of the wafer to excite metal impurity atoms to measure fluorescent X-ray generated by excitation to carry out an analysis with respect to the surface metal impurity of a measurement sample on the basis of the measured result. The term "excitation" is used in a sense to give an energy to atoms to conduct a transition thereof from the ground state to a higher energy level.

Namely, it is known that when an X-ray is incident to the material, atoms are excited, whereby a fluorescent X-ray (scattered light) is generated in addition to a reflected light. The X-ray analyzing method utilize this phenomenon. Since the light quantity of the fluorescent X-ray is proportional to the quantity of an object to be excited, the quantity of the metal impurity attached can be measured by measurement of that light quantity. Further, since the metal impurity has an energy peculiar to the object to be excited, the kind of the metal impurity is made clear by examining that energy.

As stated above, in accordance with the above-mentioned analyzing method, since an approach is not employed in analysis to utilize the harmful gas mentioned above, there is no possibility that the health of an operator is injured.

In addition, in accordance with X-ray analyzing method, an excited X-ray is caused to be partially incident onto the wafer to thereby permit implementation of the positional analysis of the wafer in-place, i.e., the analysis of the state of the in-plane distribution of the metal impurity, or the analysis where the in-plane location of the metal impurity is designated. Thus, this X-ray analyzing method makes it possible to conduct a more detailed analysis as compared to the above-mentioned chemical analyzing method. Further, since there is no destruction of a wafer used as the sample, that wafer can be used as the material of the chip, and implementation of the in-line analyzing system can be realized. For this reason, at present, the approach where the metal impurity analysis on the wafer surface is conducted by the X-ray analyzing method is being the main current.

Meanwhile, the analyzing system for carrying out this analysis is roughly composed of an X-ray source, a spectroscope, and a detector, e.g., Solid State Detector (SSD).

X-ray from the X-ray source is changed to a monochromatic X-ray, and is incident onto the wafer below an angle of total reflection. The SSD is arranged so as to avoid that reflected X-ray, but receive only a fluorescent X-ray excited and generated. A light quantity value is provided by a count value of the SSD.

In accordance with the X-ray analyzing method, however, since the wafer subject to analysis is a single crystal, there are instances where the incident X-ray causes the Bragg reflection in dependency upon the incident direction of the X-ray, and the diffracted light thereof is incident to the detector. In this case, since many light quantity values due to the diffracted light which would be the cause of noise are included in measured light quantity value at this detector, there results the problem that the sensitivity is lowered.

Further, since when an extremely intensive X-ray is incident to the detector, the dead time of the detector is prolonged, there is the problem that the measurement time becomes longer than that required owing to the light quantity of that diffracted light.

In this connection, the intensity of an incident light to the detector when the Bragg reflection takes place is 10 to 20 times larger than that when no Bragg reflection takes place. As a result, the measurement time in the former case is 2 to 10 times larger than that in the latter case.

As described above, the conventional total reflection of X-ray fluorescence analyzing system has the problem that lowered sensitivity or prolonged measurement work is caused by the Bragg reflection.

SUMMARY OF THE INVENTION

With the problems with the above-mentioned prior art in view, this invention has been made, and its object is to provide a total reflection of X-ray fluorescence analyzing system capable of immediately conducting measurement at a high sensitivity.

A total reflection of X-ray fluorescence analyzing system according to this invention includes measurement sample drive element wherein when it is assumed that the lattice interval of a measurement sample is d, the wavelength of X-ray is λ, the irradiation angle that the X-ray and the lattice plane of the measurement sample form is θ, and an arbitrary integer is n, the drive means is adapted to carry out positioning of sample points by moving the measurement sample under the state where the orientation with respect to the X-ray of the measurement sample is fixed so as to satisfy the condition described below:

$$2d \sin \theta \neq n\lambda.$$

In the total reflection of X-ray fluorescence analyzing system of this invention as the first aspect, the measurement sample drive element is adapted to conduct positioning of sample points by moving the measurement sample thus to determine, under that state, the orientation with respect to the X-ray of the measurement sample so as to satisfy the condition described below:

$$2d \sin \theta \neq n\lambda.$$

In the total reflection X-ray analyzing system of this invention as the second aspect, the measurement sample drive element includes a sample stage which can be fixed with respect to incident excited X-rays so as to satisfy the condition described below:

$$2d \sin \theta \neq n\lambda.$$

In accordance with this invention, by drawing attention to the fact that the measurement sample is a single crystal, and the direction with respect to the X-rays of the lattice plane is primarily determined by the orientation of the measurement sample, the orientation of the measurement sample is set so as to avoid the orientation in which the Bragg reflection takes place. For this reason, there is no possibility that many incident light quantity values by the Bragg reflection which would be noise are included in the measured light quantity value at the detector. Thus, high sensitivity measurement can be conducted.

In addition, since a measure is taken such that excess rays of light by the Bragg reflection is incident to the detector, it is prevented that the measurement time becomes a value larger than required. Thus, prompt measurement can be conducted.

DETAILED DESCRIPTION OF THE PREFERRED EMBODIMENTS

Preferred embodiments of this invention will now be described with reference to the attached drawings.

Figure 4:
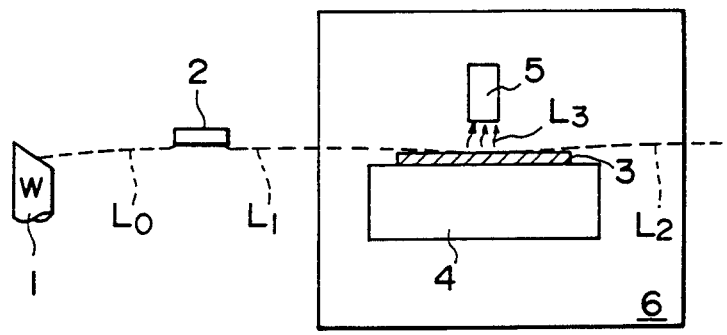
FIG. 4 is a front view schematically showing the entirety of the system shown in FIGS. 1 to 3.

In FIG. 4, reference numeral 1 denotes an X-ray source, and reference numeral 2 a monochromater. The X-ray source 1 generates continuous X-rays and characteristic X-rays of tungsten (W) as X-rays $L_0$. These X-rays $L_0$ are changed to X-rays $L_1$ of a monochromatic WL$\beta_1$ (wavelength = 1.28176 angstroms) by the monochromater 2.

Reference 3 denotes a Si wafer serving as a measurement sample, and reference numeral 4 an XY stage. The wafer 3 is horizontally mounted on the upper surface of the XY stage 4, and is fixed by means of the electrostatic chuck. The X-rays $L_1$ from the monochromater 2 are incident onto the wafer 3 wherein the incident angle $\phi 1$ is set to a total reflection angle, i.e., an angle less than a critical angle of silicon. Practically, the incident angle $\phi 1$ is an angle less than 0.2 degrees. Thus, these X-rays L; are reflected on the surface of the wafer 3, resulting in reflected X-rays $L_2$, and excite atoms on the surface of the wafer 3 to radiate fluorescent X-rays $L_3$. When there is no metal impurity on the surface of the wafer 3, a radiation wave from the silicon atoms is generated. In contrast, when there is any metal impurity on the surface of the wafer 3, a radiation wave from the atoms of the metal impurity is generated simultaneously.

Reference numeral 5 denotes a detector. This detector 5 carries out a count operation by a time corresponding to a light quantity of an incident light. The count value becomes equal to a value corresponding to an energy of an incident light.

Reference numeral 6 denotes a measurement chamber. The wafer 3, the stage 4 and the detector 5 are arranged within the measurement chamber 6. In measurement, the interior of the measurement chamber 6 is kept in a vacuum state of the order of about $10^{-2}$ Torr.

Figure 5:
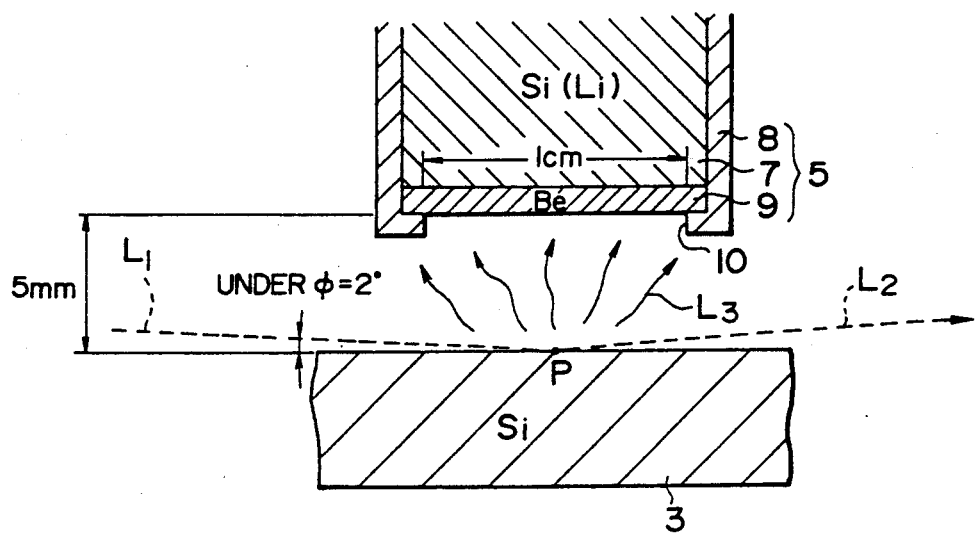
FIG. 5 is an enlarged view showing the essential part of FIG. 4.

The detector 5 is composed, as shown in FIG. 5, of a detecting element 7 comprised of a semiconductor of silicon (Si) including lithium (Li) etc., a casing 8 for accommodating the element 7, and an opening portion 10 bored in the bottom portion of the casing 8. This opening portion 10 is opened facing the wafer 3. Between the opening portion 10 and the element 7, a beryllium (Be) plate 9 is inserted. A window is constituted by the Be plate 9 and the opening portion 10. Fluorescent X-rays $L_3$ from the wafer 3 are incident to the element 7 through the window.

Between the lower end of the opening portion 10 and the upper surface of the wafer 3, there is provided a gap for permitting X-rays $L_1$ and $L_2$ to be passed therethrough. This gap is set as small as possible in order to increase the detection sensitivity. In this embodiment, the gap is 5 mm.

The diameter of the opening portion 10 is set to 1 cm in the embodiment. Light in the range from a vertical direction to a direction inclined by 45 degrees thereto when viewed from the measurement position (i.e., the incident position of the X-ray $L_1$) indicated by reference Symbol P in FIG. 5 is permitted to be passed through the opening portion 10.

The element 7 outputs a signal of the voltage level corresponding to an incident light quantity to deliver it to a voltage controlled counter (not shown) which carries out a count operation by a time corresponding to the input voltage level.

Figure 1:
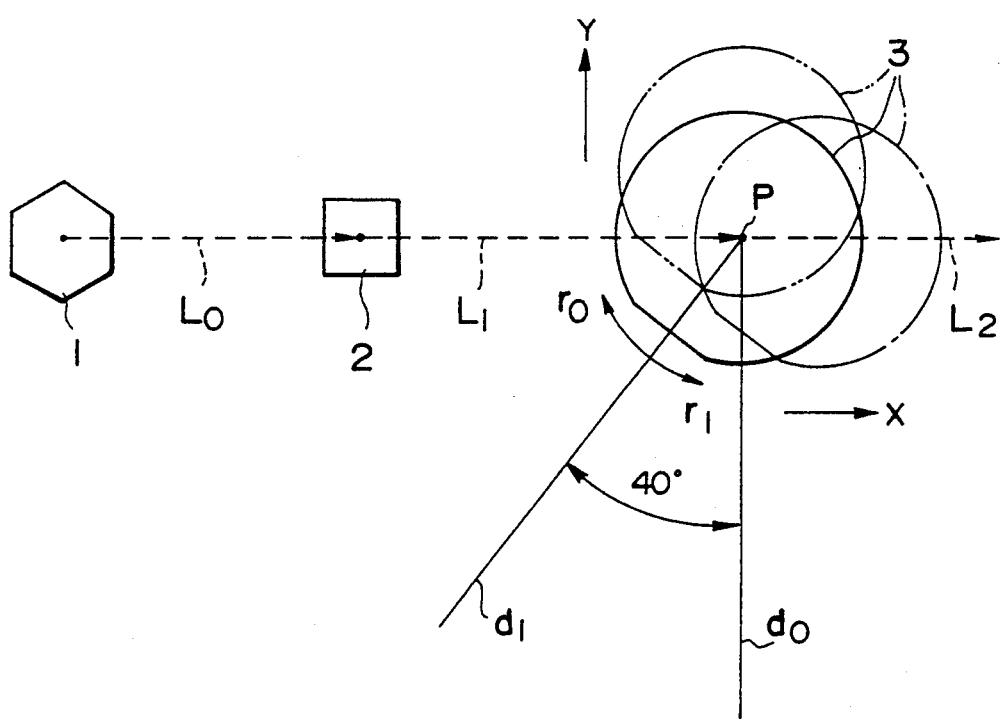
FIG. 1 is an explanatory view showing the essential part of a total reflection of X-ray fluorescence analyzing system according to a first embodiment of this invention.

FIG. 1 is an explanatory view showing the essential part of a system according to a first embodiment of this invention.

As shown in this figure, the Si wafer 3 is rotated as indicated by arrows $r_1$ and $r_0$ by the rotation of the XY stage 4. Thus, the orientation with respect to the X-rays $L_1$ is set. In the state where the orientation is fixed, the Si wafer 3 is moved in a two-dimensional manner by horizontal movement in the X- and Y- directions of the XY stage 4. Thus, respective sample points of the Si wafer 3 are subjected to positioning so that they are located at the measurement position P.

Assuming now that the lattice interval of the wafer 3 is d, the wavelength of the X-ray $L_1$ is $\lambda$, the incident angle that the X-ray $L_1$ and the lattice plane of the wafer 3 form is $\theta$, and an arbitrary integer is n, the orientation with respect to the X-ray $L_1$ of the wafer 3 is set so as to satisfy the following condition:

$$2d \sin \theta \neq n\lambda \quad (1)$$

In accordance with this setting method, the above equation (1) is first transformed so as to delete $\theta$ in the above equation (1) to determine $\theta$ by the following equation:

$$\theta = \sin^{-1}(n\lambda/2d)$$

Thus, an angle where the Bragg diffraction takes place is determined.

If the crystal orientation of the wafer is that of four-fold axis of symmetry, the positions rotated in succession by 90 degrees from the determined angle are considered as the position where the Bragg reflection is strong. Namely, in the case of Si wafer having, e.g., the lattice plane (100), four positions of the position of zero degrees which is the center position of the orientation flat, and positions rotated in succession by 90 degrees from the angle, i.e., positions of 90, 180 and 270 degrees are considered as the position where the Bragg reflection is strong. After estimation is roughly conducted by using the equation in a manner stated above, when X-ray $L_1$ is caused to be incident to the peripheral position thereof in various orientations, orientations desired to be avoided because the Bragg reflection is strong are made clear.

Accordingly, it is seen that it is sufficient to determine the orientation of the wafer 3 in order to avoid such undesired directions found out in a manner stated above.

The sample points of the wafer 3 are, adapted to be subjected to positioning by horizontally moving the XY stage in X- and Y- directions under the state where the orientation with respect to the X-ray $L_1$ is fixed.

As stated above, since the state where no Bragg reflection takes place is kept during measurement, the possibility that many incident light quantity values due to the Bragg reflection which would be the cause of noise are included in the measured light quantity values at the detector 5. Thus, high sensitivity measurement can be conducted.

Further, since there is employed an arrangement such that excess light rays due to the Bragg reflection are prevented from being incident to the detector 5, it can be prevented that it takes a measurement time longer than a time required. Thus, prompt measurement can be conducted.

The result of the comparative test between the conventional system and the system of this embodiment which has been conducted in connection with the Si wafer of the crystal orientation (100) is shown as an example. In this embodiment, the distribution measurement of the metal impurity is conducted in connection with 21 sample points on the surface of the wafer 3 wherein the measurement time is set to one hour and half (about 250 seconds per each point) as a set value.

Initially, in the case of the conventional system, by moving the wafer 3 in X- and Y- directions and rotating it in a $r_0$-$r_1$ direction, those sample points are subjected to positioning.

The result in the case where such a test is conducted with the conventional system is as follows. When the measurement proceeds up to the 12 sample points, the rate of occurrence of miscount at respective points, i.e., the rate where miscount takes place because the incident light level is high and the count operating time is therefore insufficient in the case of the above-mentioned 250 seconds becomes equal to 50 to 90%. As a result, the measurement time was prolonged. It took about eight hours until the measurement of all sample points is completed.

The measurement method of the wafer 3 in the system of this embodiment will now be described.

Figure 6:
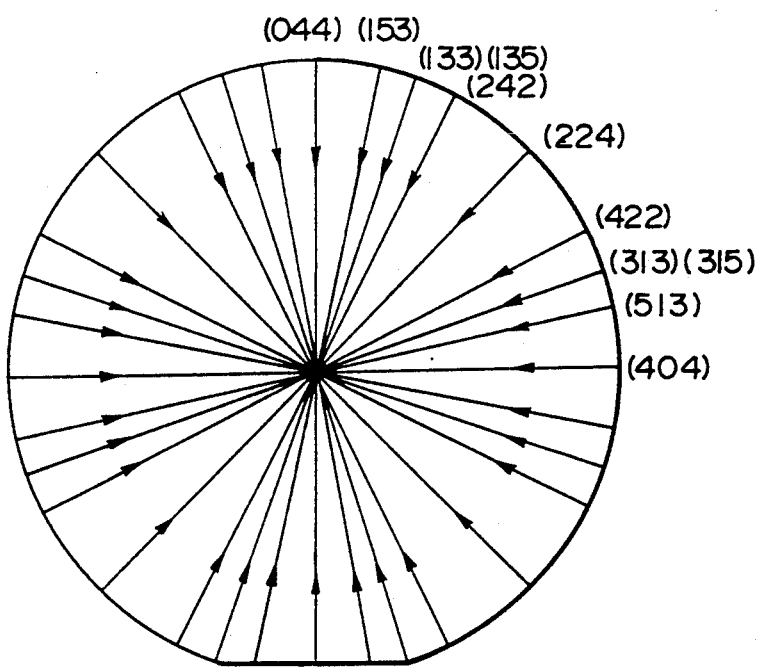
FIG. 6 is an explanatory view of an incident direction in which the Bragg reflection of W-L$\beta_1$ takes place.

FIG. 6 shows the orientations, each indicated by an arrow and shows the lattice planes which cause diffraction, each indicated by (hK1), in which an intensive diffracted light is caused to be incident to the detector wherein these orientations are obtained as the result of the fact that X-rays $L_1$ are caused to be incident to the wafer 3 in various orientations.

It is seen from FIG. 6 that lines of the arrows concentrate on the position of the four-fold axis of symmetry of silicon having the crystal orientation (100).

Figure 7:
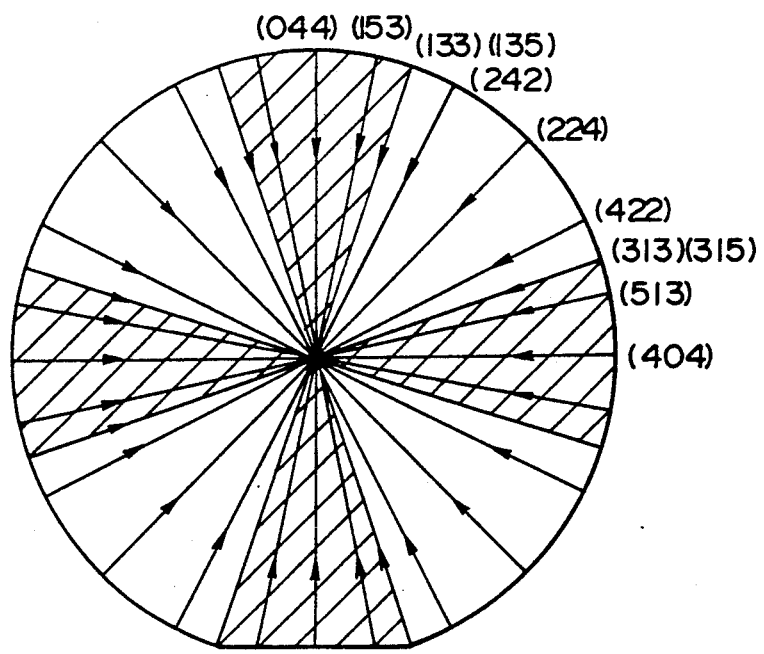
FIG. 7 is an explanatory view of an incident direction in which an intensive Bragg reflection takes place.

Further, when careful examination is made in connection with the area where there concentrate lines indicating the orientations in which an intensive diffracted light is caused to be incident to the detector 5, it has been made clear that the Bragg reflection is apt to particularly occur in the hatched areas of FIG. 7. In addition, it is seen that if there are adopted directions rotated by about 50 degrees from the center of the orientation flat of the wafer 3 as an example, there results a less diffraction.

In view of this, the wafer 3 is attached at first on the stage 4 at the orientation where the center of the orientation flat of the wafer is on the directional line $d_0$ thereafter to rotate the stage 4 by about 40 degrees in a $r_0$ direction to set the orientation of the wafer 3.

In this state, the stage 4 is moved in X- and Y-directions to allow respective sample points of in-plane 21 points of the wafer 3 to be subjected to positioning so that they are located at the measurement position P, thus to carry out measurement.

In accordance with the system of the first embodiment, all measurements are completed only within one hour and half.

Figure 8:
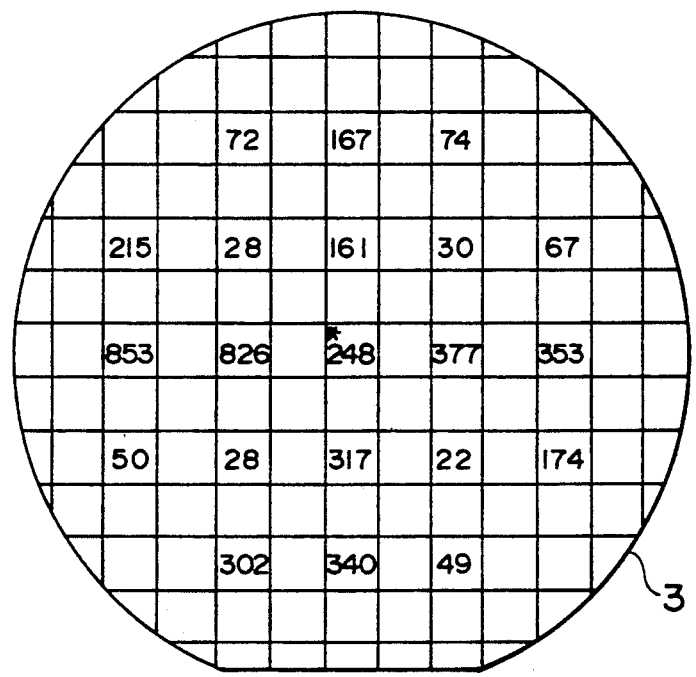
FIG. 8 is a wafer in-plane distribution diagram of measured values by the conventional analyzing system.
Figure 9:
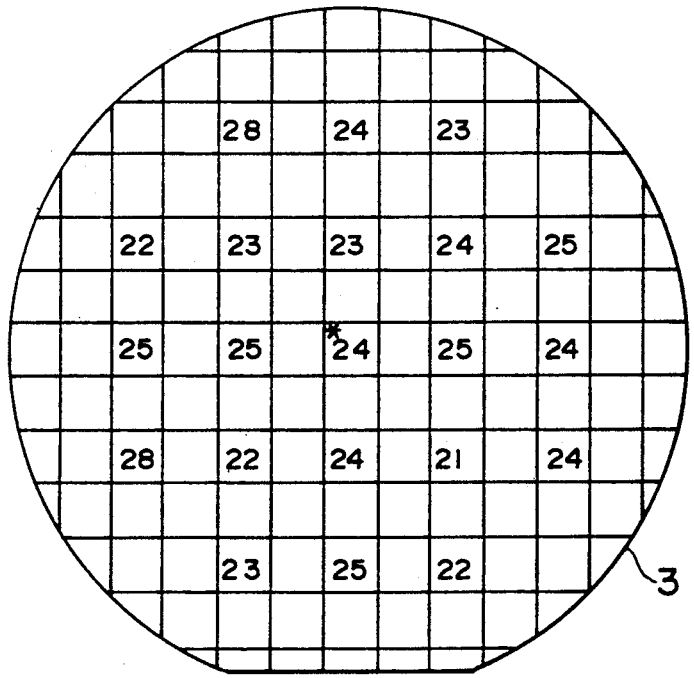
FIG. 9 is a wafer in-plane distribution diagram of measured values by the system shown in FIGS. 1 to 5.

FIG. 8 shows count values per unit time at respective sample points by the conventional system and FIG. 9 shows count values per unit time at respective sample points by the system of the first embodiment. It is seen from these figures that, in the case of the conventional system, the count value is extremely high at the sampling point corresponding to the regions where the above-mentioned diffraction takes place, whereas, in the case of the system of the first embodiment, mean values appear at the respective sample points.

Figure 10:
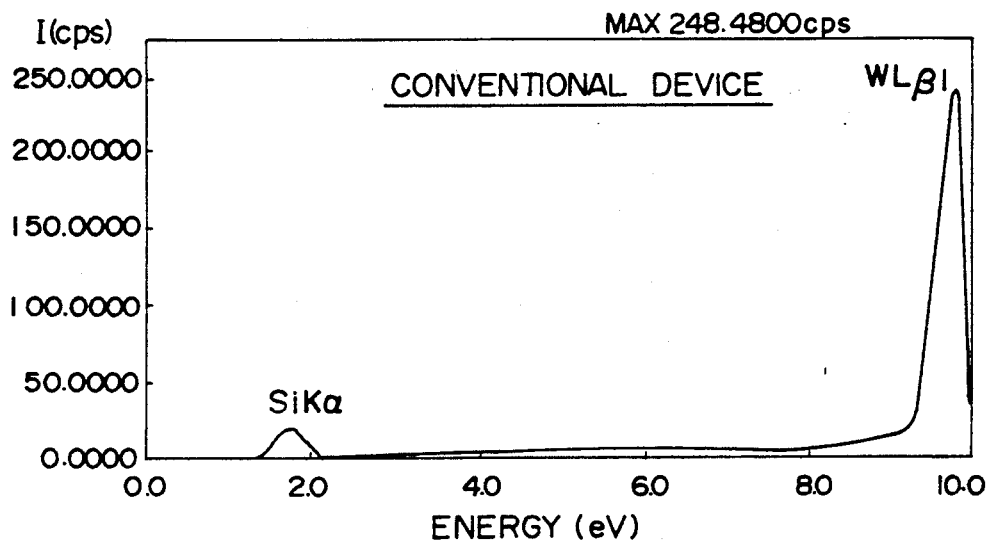
FIG. 10 is a spectrum explanatory view of sampling points to which * is attached in FIG. 6.
Figure 11:
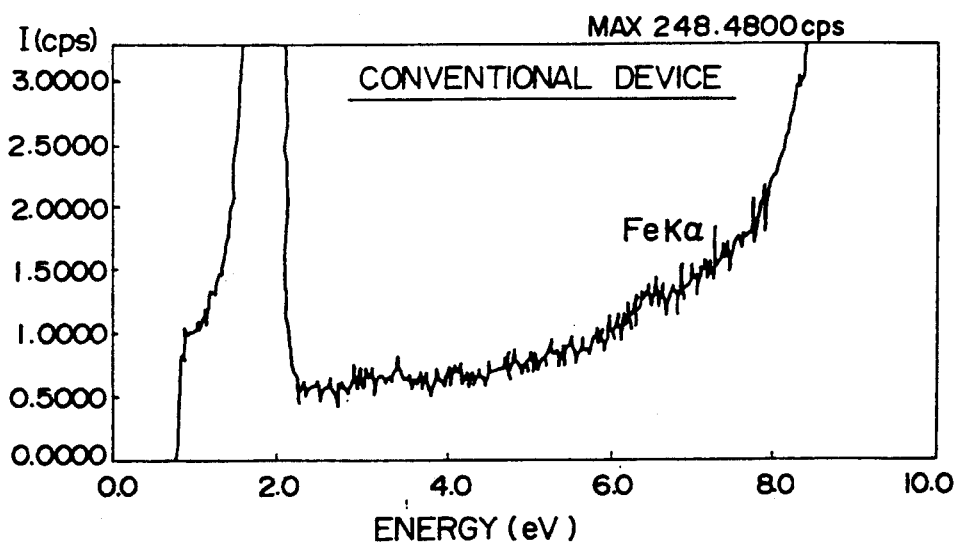
FIG. 11 is an enlarged view of FIG. 10.
Figure 12:
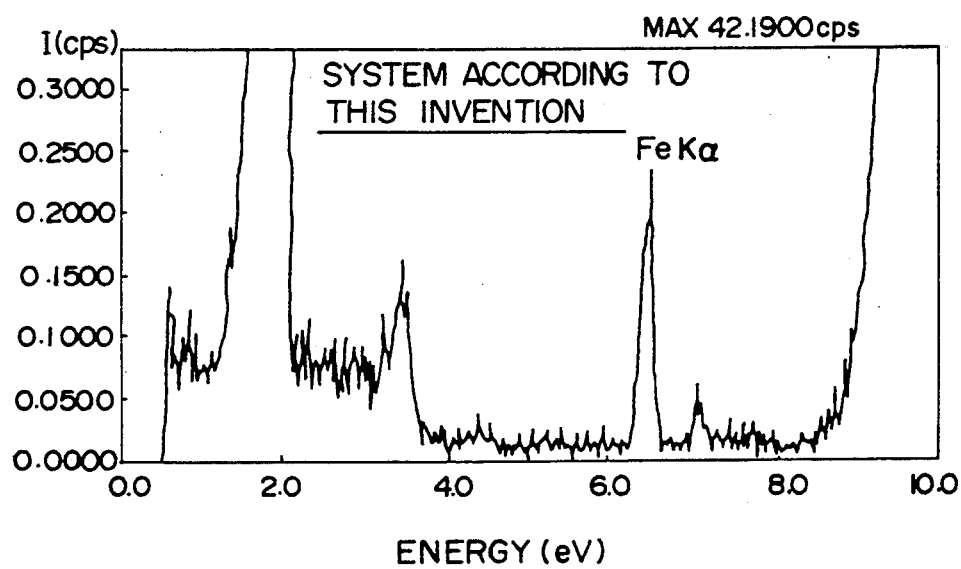
FIG. 12 is a spectrum explanatory view of sample points to which * is attached.

Further, FIG. 10 is a curve showing a spectrum with respect to the sample points to which the symbol * is attached in FIG. 8, FIG. 11 is a curve diagram obtained by enlarging the scale of FIG. 10, and FIG. 12 is a curve the spectrum with respect to sample points to which the symbol * is attached in FIG. 9.

First, when attention is drawn to FIG. 11, the maximum count value is equal to 248.4000 cps. This value is extremely high as compared to 42.1900 cps of FIG. 12. The measurement time is prolonged accordingly.

Although the count value is high as stated above, there cannot be found out a peak in the spectrum region (corresponding to a wavelength having an energy $E = C \cdot K / \lambda$ (C is light velocity and K is constant). In view of this, the figure obtained by enlarging the scale is FIG. 11. From this figure, there appears a weak peak in the vicinity of the energy (about 6.4 KeV) of the fluorescent X-ray of Fe, but that peak cannot be clearly recognized. Namely, this mean that the sensitivity is low.

Turning now to FIG. 12, it is seen that the maximum count number is low as stated above and therefore the count operation is efficiently performed.

Further, the peak of Fe was discriminated, and it was confirmed by measurement that the concentration of Fe is $3 \times 10^{10}$ to $5 \times 10^{10}$ [atoms/cm$^2$].

As stated above, in accordance with the system of the first embodiment, high sensitivity and prompt measurement can be conducted.

Figure 2A:
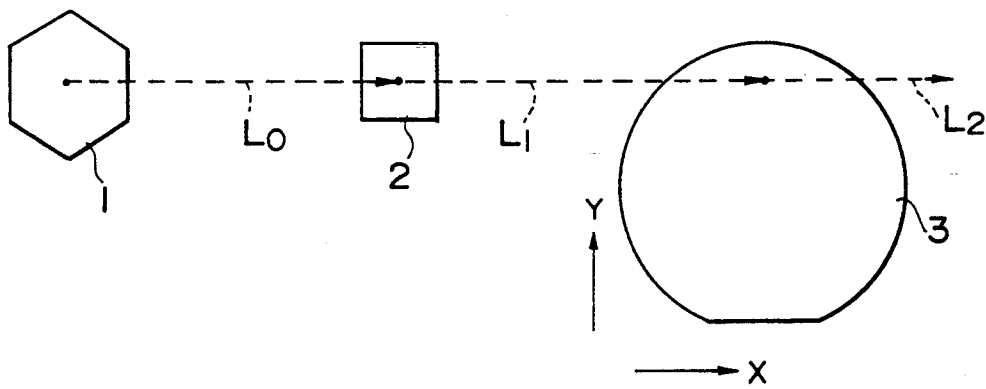
FIGS. 2A and 2B are explanatory views respectively showing the essential part of a total reflection of X-ray fluorescence analyzing system according to a second embodiment of this invention.
Figure 2B:
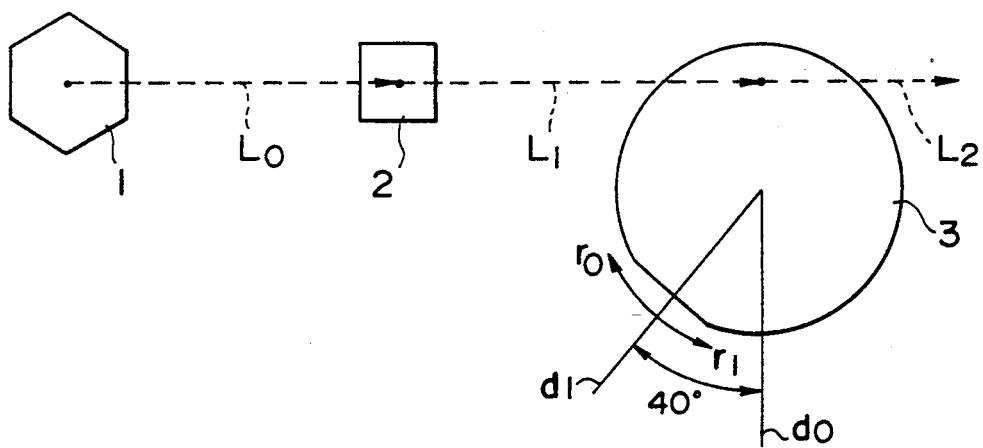

FIGS. 2A and 2B are explanatory views respectively showing the essential part of a system according to a second embodiment of this invention.

In the system shown in FIG. 1, the wafer 3 is first rotated in a $r_0$–$r_1$ direction where the orientation with respect to the incident X-ray $L_0$ is fixed, and then moved in X- and Y- directions to position the wafer 3.

On the contrary, in the case of the stage 4 shown in FIGS. 2A and 2B, as shown in FIG. 2A, the wafer 3 is first moved in X- Y- directions to allow the sample points to be subjected to positioning to rotate the wafer 3 in a $r_0$–$r_1$ direction under that state so as to satisfy the condition of 2d sin $\theta \neq n\lambda$ to determine the orientation with respect to the incident X-ray $L_0$ as shown in FIG. 2B.

Also in the case where the orientation determination test of this embodiment is conducted, satisfactory result was obtained. In this case, the stage 4 is first moved in X- and Y- directions to allow respective sampling points of in-plane 21 points of the wafer 3 to be subjected to positioning so that they are located at the measurement point P to attach, under this state, the wafer 3 on the state 4 as a temporary measure at the orientation where the center of the orientation flat is positioned on the directional line $d_0$ thereafter to rotate the stage 4 by about 40 degrees in a $r_0$ direction to set the orientation of the wafer 3, thus to conduct a measurement.

Figure 3:
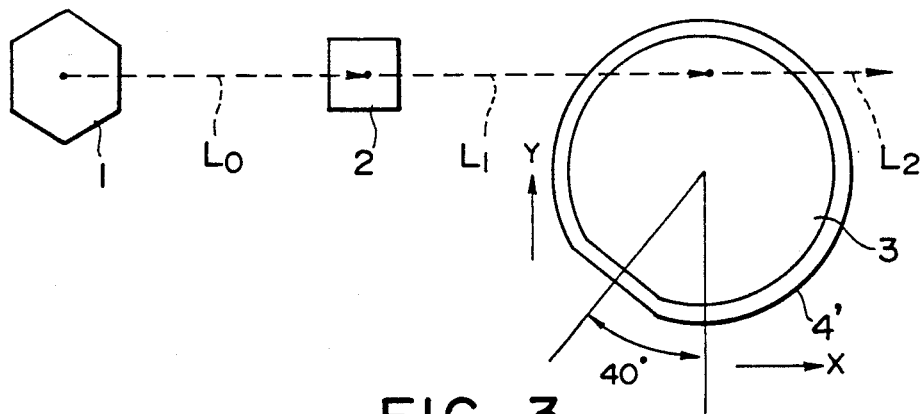
FIG. 3 is an explanatory view showing the essential part of a total reflection of X-ray fluorescence analyzing system according to a third embodiment of this invention.

FIG. 3 is an explanatory view showing the essential part of a total reflection of X-ray fluorescence analyzing system. Namely, it is additionally described by this embodiment that the stage for positioning of sample points and the stage for determination of orientation may be conducted in an arbitrary order, i.e., this invention holds irrespective of whether or not either of these stages is conducted precedingly or succeedingly.

The total reflection X-ray analyzing system shown in FIG. 3 is characterized in that the system includes a sample stage 4' fixed with respect to an incident excited X-ray so as to satisfy the condition of 2d sin $\theta \neq n\lambda$. This stage 4' includes a linear side edge corresponding to the orientation flat of the wafer 3. When the wafer 3 is set on the stage 4' in a manner that the direction of the side edge and the direction of the orientation flat of the wafer 3 are in correspondence with each other, the orientation of the wafer 3 is automatically determined.

In the case of this embodiment, after the wafer 3 is set in this way, the stage 4' is driven in X- and Y-directions to allow the sample points to be subjected to positioning. It is to be noted that the stage 4' of the embodiment is not necessarily required to be driven in the $r_0$–$r_1$ direction. There may be employed an arrangement such that the stage 4' is driven only for adjustment. In addition, an arrangement such that adjustment can be manually made is basically sufficient for this purpose.

As described above, in accordance with this invention, by drawing attention to the fact that the measurement sample is a single crystal, and the direction with respect to the X-ray of the lattice plane is primarily determined by the orientation of the measurement sample, the orientation of the measurement sample is set so as to avoid the orientations where the Bragg reflection takes place. Accordingly, the possibility that many incident light quantity values due to the Bragg reflection which would be the cause of noise are included in the measured light quantity values at the detector is eliminated. Thus, high sensitivity measurement can be conducted.

In addition, since there is employed an arrangement such that excess rays of light due to the Bragg reflection are prevented from being incident to the detector, it is prevented that it takes for measurement a time more than required. Thus, prompt measurement can be conducted.

What is claimed is:

1. A system for carrying out an analysis with respect to a metal impurity on the surface of a single crystal semiconductor by using total reflection of an X-ray fluorescence said system comprising:
incident means for allowing X-ray to be incident onto the surface of the single crystal semiconductor serving as a measurement sample to be analyzed at an incident angle less than a total reflection angle as a critical angle peculiar to a material constituting said semiconductor;
fixing means wherein when it is assumed that said semiconductor surface is partitioned by a lattice having a specific interval d, and that a wavelength of said X-ray caused to be incident by said incident means is $\lambda$, an incident angle that said X-ray and said semiconductor surface form is $\theta$, and an arbitrary integer is n, said fixing means for movably mounting said crystal to fix a crystal orientation of said semiconductor with respect to said X-ray so as to satisfy the condition of "2d sin $\theta \neq n\lambda$";

positioning means for allowing sample points to which said X-ray is incident to be subjected to positioning by horizontally moving said semiconductor so as to satisfy said condition of "2d sin $\theta \neq n\lambda$"; and analyzing means for measuring a light quantity of a fluorescent X-ray generated as the result of the fact that said X-ray incident at said incident angle excites atoms at the surface of said single crystal semiconductor to thereby analyze a quantity of the metal impurity attached on said semiconductor surface under the condition where the Bragg reflection causing measurement noises does not take place.

2. A system as set forth in claim 1, wherein said single crystal semiconductor serving as said measurement sample is formed as a complete single crystal in the form of a thin plate, and is composed of a silicon (Si) wafer having a crystal orientation (100).

3. A system as set forth in claim 2,
wherein said fixing means is comprised of a rotation mechanism on which said wafer is mounted, said rotation mechanism being adapted to rotate said wafer to fix orientation so as to satisfy said condition, and wherein said positioning means is comprised of an XY table in which said rotation mechanism is assembled, said positioning means being adapted to horizontally move said wafer in X- and Y- directions under the state where orientation is fixed to allow a plurality of sample points of said wafer to be subjected to positioning.

4. A system as set forth in claim 3, wherein the orientation of said wafer fixed by rotation of said wafer by said rotation mechanism is four orientations of 0, 90, 180 and 270 degrees of a (100) Si wafer.

5. A system as set forth in claim 2,
wherein said positioning means is comprised of a stage for horizontally moving said wafer mounted thereon in X- and Y- directions to allow a plurality of sample points to be subjected to positioning, and wherein said fixing means is comprised of a rotation mechanism attached on said stage to rotate said stage to fix the orientation of said wafer so as to satisfy said condition.

6. A system as set forth in claim 2,
wherein said positioning means and said fixing means is comprised of a sample stage including a side edge corresponding to an orientation flat of said wafer as said single crystal semiconductor, and for allowing said wafer to be subjected to positioning and fixing it so that an incident angle of an X-ray for excitation incident onto said wafer mounted so that the direction of said side edge and that of said orientation flat are in correspondence with each other satisfies the condition of "2d sin $\theta \neq n\lambda$".

* * * * *